(12) United States Patent
Kingsley

(10) Patent No.: US 7,807,190 B2
(45) Date of Patent: Oct. 5, 2010

(54) METHODS FOR ERADICATING LICE AND FLEAS FROM A HOST

(75) Inventor: Joe D. Kingsley, Castle Valley, UT (US)

(73) Assignee: DMA International, Inc., Moab, UT (US)

( * ) Notice: Subject to any disclaimer, the term of this patent is extended or adjusted under 35 U.S.C. 154(b) by 121 days.

(21) Appl. No.: 12/140,179

(22) Filed: Jun. 16, 2008

(65) Prior Publication Data

US 2009/0312431 A1 Dec. 17, 2009

(51) Int. Cl.
*A01N 25/00* (2006.01)
*A61K 36/00* (2006.01)

(52) U.S. Cl. ...................... 424/405; 424/725

(58) Field of Classification Search ........................ None
See application file for complete search history.

(56) References Cited

U.S. PATENT DOCUMENTS

| | | | |
|---|---|---|---|
| 5,227,163 A | 7/1993 | Eini et al. | |
| 5,411,992 A | 5/1995 | Eini et al. | |
| 5,599,803 A * | 2/1997 | Hainrihar et al. | 514/70 |
| 5,858,383 A | 1/1999 | Precopio | |
| 5,902,595 A | 5/1999 | Burklow et al. | |
| 6,160,014 A * | 12/2000 | Kawada et al. | 514/535 |
| 6,350,724 B1 | 2/2002 | Kiel et al. | |
| 6,607,716 B1 | 8/2003 | Smith et al. | |
| 6,969,522 B2 | 11/2005 | Bessette | |
| 6,974,584 B2 | 12/2005 | Bessette | |
| 7,282,211 B2 | 10/2007 | Ping | |
| 2007/0020304 A1 | 1/2007 | Tamarkin et al. | |
| 2007/0077262 A1 | 4/2007 | Scialdone | |
| 2008/0118585 A1 | 5/2008 | Nouvel | |
| 2008/0145462 A1 | 6/2008 | Enan | |

* cited by examiner

*Primary Examiner*—Patricia Leith
(74) *Attorney, Agent, or Firm*—Kirton & McConkie; David B. Tingey

(57) ABSTRACT

A composition and method for eliminating foreign bodies from a host. The composition include active ingredients of menthol, camphor, and capsaicin, as well as additional components including aloe vera extract, carbomer, decyl polyglucose, deionized water, grapefruit seed extract, green tea extract, orange peel extract, queen of the prairie extract, rose water, silica, sodium, hydroxymethyl glycinate, vegetable glycerin, witch hazel, and yucca extract. The composition kills and eradicates the foreign bodies providing relief to the host.

26 Claims, 3 Drawing Sheets

METHODS FOR ERADICATING LICE AND FLEAS FROM A HOST

BACKGROUND OF THE INVENTION

1. Field of the Invention

The present invention relates to eradicating foreign bodies from a host. In particular, at least some embodiments of the present invention relate to systems and methods for eliminating fleas, lice and other foreign bodies from humans, animals and/or other hosts where such foreign bodies reside.

2. Background and Related Art

Dealing with lice, fleas, and other similar pests can be enervating, annoying, and sometimes even threatening to one's health. Specifically, lice (singular: louse) are an order of over 3000 species of wingless parasitic insects and are ectoparasites of mammals and birds. In a human, the head louse lives among hairs and feeds on extremely small amounts of blood drawn from the scalp. The eggs (nits) of the head louse are white and can be seen with the naked eye. Lice are a problem, especially for children ages three to twelve years of age, and for girls more often than boys. The bites cause a scalp to unnervingly itch and become inflamed. In fact, persistent scratching results in skin irritation and even infection. Lice do not spread disease, but they are contagious. They can be contracted through brief skin contact, and also by borrowing 'contaminated' clothes and towels. Lice are detected by noticing itchiness and when looking at a lice-infested scalp, small grains attached to the hair roots on the head are visible, as well as by red, itchy spots.

Lice are problematic in school-age children because a child with lice is usually sent home from school. This embarrasses the child and his or her parents, and compromises the child's learning for the missed days. Additionally, lice are becoming resistant to traditional remedial techniques and medications, which further compromises school attendance and consumes the time of school nurses, school officials, and parents.

Many products currently available to eliminate lice are insecticides, so special care is required to reduce risk of toxicity. Additionally, combing the hair with nit combs or fine-toothed combs, or physically picking out the nits may also be necessary. Moreover, most infestations of lice require vigilant and ongoing cleaning of the house, clothes, bed linen, couch covers, towels, etc. Such actions might be repeated and necessary for as much as three weeks post infestation.

Unfortunately, lice are becoming resistant to even the strongest medications and treatments. For instance, the effectiveness of one popular product used to eradicate lice was investigated by the Harvard School of Public Health. Studies found that according to entomologists, the molecules in permethrin and pyrethrin, two components of this popular lice medication, were so similar that crossover resistance was almost certain.

Fleas are similarly problematic. Fleas are wingless, jumping parasites which, like mosquitoes and lice, feed on blood. Fleas, in contrast, are spread mainly through pets. A human may get fleas and becomes aware of them because a flea bite is painful and quickly starts to itch. Because fleas cannot fly, bites appear mostly around the ankles and are recognized by small red blotches on the skin. Similar to lice, ridding a host of fleas requires diligence, patience, and time, typically require several weeks of effort and treatment.

While techniques currently exist that are used to treat individuals for dealing with lice, fleas, and other similar pests, challenges still exist. Accordingly, it would be an improvement in the art to augment or even replace current techniques with other techniques.

SUMMARY OF THE INVENTION

The present invention relates to eradicating foreign bodies from a host. In particular, at least some embodiments of the present invention relate to systems and methods for eliminating fleas, lice and other foreign bodies from humans, animals and/or other hosts where such foreign bodies reside.

Implementation of the present invention takes place in association with the use of various natural additives to eliminate foreign bodies, such as fleas, lice, and the like, from a host body, such as a human or animal body. In at least some implementations of the present invention, the composition is in the form of a product sold under the trademark SORE NO MORE!™ and is used in accordance with embodiments of the present invention to eliminate fleas, lice and other foreign bodies from humans, animals and/or other hosts where such foreign bodies reside. The SORE NO MORE!™ product is available from the www.sorenomore.com website at 150 East Center Street, Moab, Utah 84532.

In some implementations of the present invention, the composition is applied to a host on areas affected or infested with foreign bodies. The composition may be in the form of, but not limited to, a gel, a lotion, a shampoo, or another medium so that it may be externally and topically applied. The composition is allowed to remain on the infested area a suitable amount of time to completely kill the foreign bodies. The affected or infested area is then washed or rinsed to remove the foreign bodies from the area.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

Figure 1:
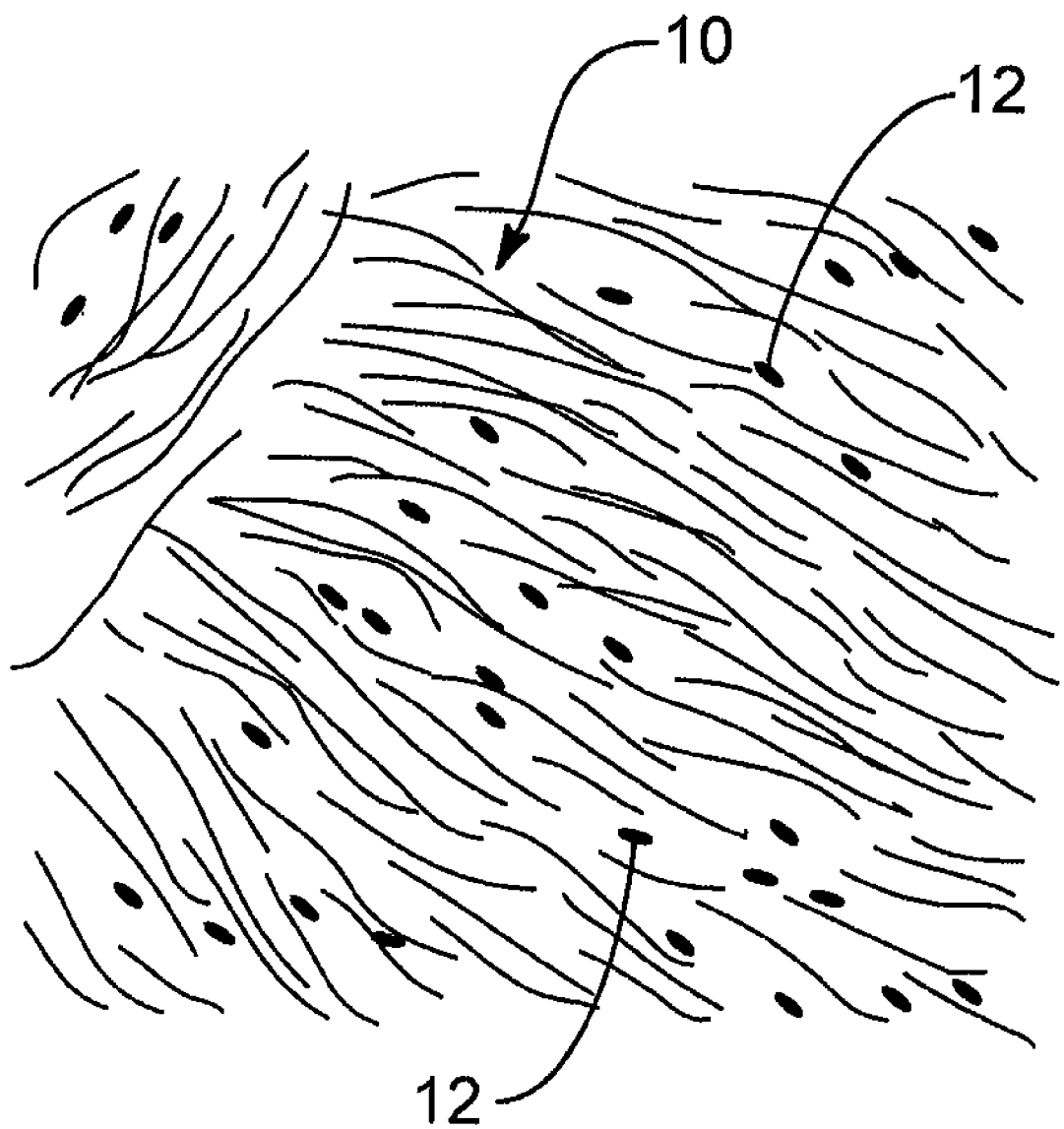
FIG. 1 illustrates a host infested with a foreign body, specifically a human scalp infested with lice.

The present invention relates to eradicating foreign bodies from a host. In particular, at least some embodiments of the present invention relate to systems and methods for eliminating fleas, lice and other foreign bodies from humans, animals and/or other hosts where such foreign bodies reside.

Embodiments of the present invention embrace the use or application of a composition having menthol, camphor, and/or capsaicin as active ingredients. In further embodiments, the one or more active ingredients are further combined with at least one of aloe vera extract, carbomer, decyl polyglucose, deionized water, grapefruit seed extract, green tea extract, orange peel extract, queen of the prairie extract, rose water, silica, sodium, hydroxymethyl glycinate, vegetable glycerin, witch hazel, and yucca extract to eliminate foreign bodies, such as fleas, lice, and the like, from a host body, such as a human or animal body.

In at least some embodiments of the present invention, the composition is in the form of a product sold under the trademark SORE NO MORE!™ and is used in accordance with embodiments of the present invention to eliminate fleas, lice and other foreign bodies from humans, animals and/or other hosts where such foreign bodies reside. The SORE NO MORE!™ product is available from the www.sorenomore.com website at 150 East Center Street, Moab, Utah 84532.

Traditionally, the product and composition above, or the combination of aforementioned ingredients, is used to alleviate pain. Specifically, certain plant extracts are combined with certain active ingredients resulting in an analgesic gel that provides temporary relief to those suffering minor aches and pains. It works by massaging the combination of ingredients onto an affected area and it is especially useful for those with arthritis, backaches, strains, bruises, and sprains and has unique heating and cooling properties.

In a preferred embodiment, the combination of capsaicin, camphor and menthol, as active ingredients, and Aloe Vera Extract, Carbomer, Decyl Polyglucose, Deionized Water, Grapefruit Seed Extract, Green Tea Extract, Orange Peel Extract, Queen of the Prairie Extract, Rose Water, Silica, Sodium Hydroxymethyl Glycinate, Vegetable Glycerin, Witch Hazel, and Yucca Extract as inactive ingredients, is useful in eradicating certain foreign bodies, such as, but not limited to fleas and lice, from a host, such as but not limited to humans, animals and other mammals.

More specifically, in at least one embodiment of the present invention, the composition comprises three-percent Menthol, three-percent Camphor, and 0.03% Capsaican with Aloe Vera Extract, Carbomer, Decyl Polyglucose, Deionized Water, Grapefruit Seed Extract, Green Tea Extract, Orange Peel Extract, Queen of the Prairie Extract, Rose Water, Silica, Sodium Hydroxymethyl Glycinate, Vegetable Glycerin, Witch Hazel, and/or Yucca Extract. While some embodiments embrace three-percent Menthol, three-percent Camphor, and 0.03% Capsaican, other embodiments embrace other percentages of Menthol, Camphor, and/or Capsaicin.

The composition is then used on the host on areas affected or infested with foreign bodies. The composition may be in the form of, but not limited to, a gel, a lotion, a shampoo, or another medium so that it may be externally and topically applied. In at least some implementations, it is applied so that it is absorbed or at least rubbed in thoroughly. The composition is allowed to remain on the infested area a suitable amount of time for it to completely kill and eradicate all adult lice and lice eggs. Similarly, the composition is equally effective at killing and eradicating fleas and flea eggs when applied to an infested animal. The affected or infested area is then washed or rinsed thereby removing the foreign bodies from the treated area. At least one embodiment is water soluble, such that the composition can be applied to an infested area, and subsequently removed with water or other liquids with properties similar to water, thereby removing the unwanted foreign bodies. Specifically, the composition disrupts the protective cellular structure of the eggs, nits, and fleas resulting in cellular death. Additionally, the composition suffocates the foreign bodies thereby restricting their propagation and resulting in cellular death. After the infected area is treated with the composition, the dead, unwanted foreign bodies are removed from the host by rinsing the host with water, or another suitable rinsing agent. Generally, the composition is effective with one application as described above. However, in rare cases of severe infestation, the composition is applied up to three times for complete eradication. Accordingly, at least some embodiments of the present invention embrace an improved composition or formulation for complete extirpation of foreign bodies from a host.

In at least one embodiment, the composition contains no waxes, oils, artificial colors or other harmful chemicals. Accordingly, it is safer than most insecticides or pesticides commonly used for lice or flea elimination. Generally, the composition is safe for external use only and application of the compound to open cuts or wounds should be avoided. However, in the event that an animal licks the applied compound, the compound is generally safe against this type of exposure. Additionally, the lack of waxy, oily or artificial color additives ensures that the composition completely washes out hair with no residual stains or residues.

While the methods and processes of the present invention have proven to be particularly useful in the area of eradicating fleas and lice, those skilled in the art can appreciate that the methods and processes can be used in a variety of different applications and in a variety of different compositions to prevent and/or eradicate foreign bodies from a host, such as a human, animal or other host.

It is emphasized that the present invention may be embodied in other forms. For example, the present invention may be used in conjunction with another product to treat additional symptoms of the host. In one embodiment, the composition of the present invention is used in conjunction with a cleansing shampoo. In another embodiment, the composition of the present invention is used in conjunction with a hair conditioning solution. In yet another embodiment, the composition of the present invention is used in conjunction with an antibiotic. Thus, neither the drawings nor the following more detailed description of the various embodiments of the system and method of the present invention limit the scope of the invention. The drawings and detailed description are merely representative of examples of embodiments of the invention; the substantive scope of the present invention is limited only by the appended claims recited to describe the many embodiments. The various embodiments of the invention are best understood by reference to the drawings, wherein like elements are designated by like alphanumeric character throughout.

Referring now to FIG. 1 a host 10 is shown as infested with a foreign body 12. Specifically, FIG. 1 illustrates a human scalp 10 infested with lice 12. As previously discussed, lice 12 are parasitic foreign bodies that feed themselves on the blood of the host 10. The louse 12 access the blood of the host 10 by biting the host 10. Therefore, the lice 12 typically will infest highly vascular areas of the host 10. Additionally, the eggs, or nits of the lice 12 require warmth and moisture to hatch. As such, the human head 10 is an ideal breeding ground for lice 12.

The human head is highly vascular and therefore substantially warmer as compared to other regions of the human body. The scalp of the human head further includes high concentrations of sweat glands to aid in regulating the temperature of the host. As such, the human scalp is sufficiently warm and moist so as to provide a preferred breeding ground for the louse 12. Lice 12 lay approximately 6-8 eggs each day and require approximately five blood meals each day to survive. Each of these blood meals requires the lice 12 to break the skin of the host 10. These bites commonly result in itching and rashes to the host 10. As such, the host 10 will commonly scratch the bites causing open sores on the host 10. These sores can subsequently become infected with bacteria and fungi.

Figure 2:
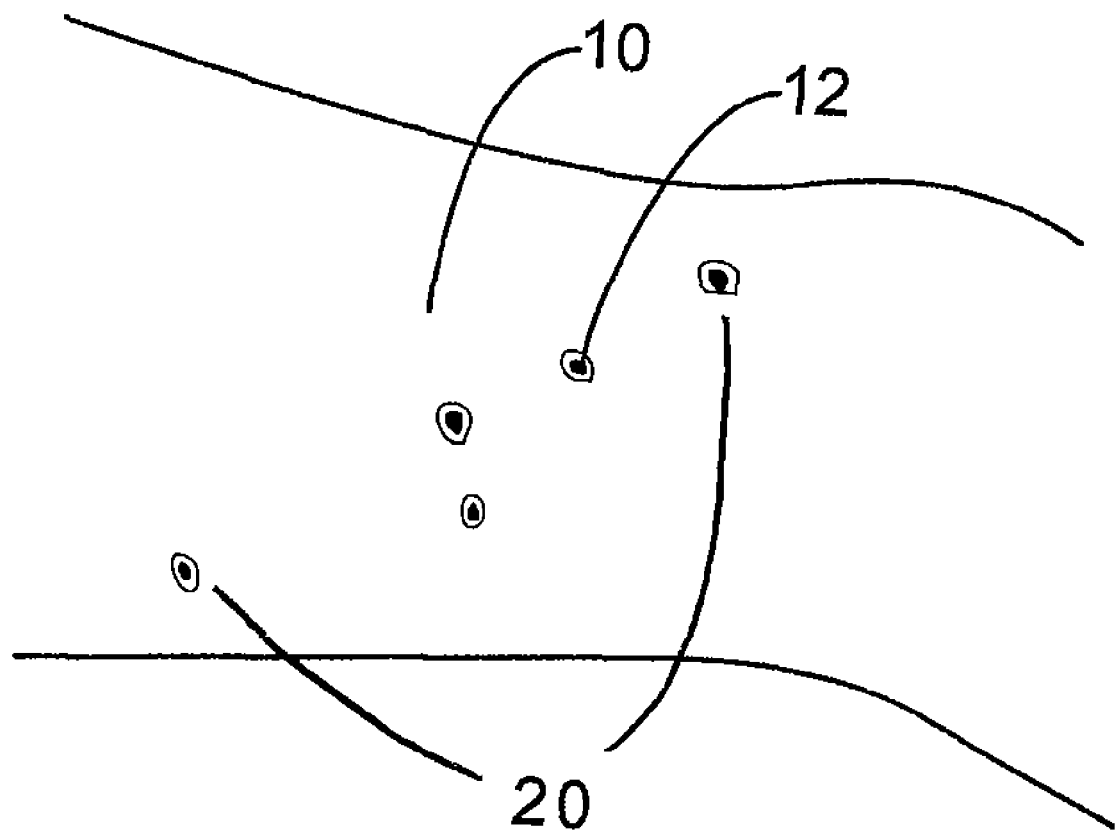
FIG. 2 illustrates flea bites on a human host.

In addition to lice 12, other parasitic foreign bodies may infest a host thereby causing itching and irritation. Referring now to FIG. 2 a host (a human) 10 having flea bites 18 is shown. Flea bites 18 are most common on areas of the body with tight clothing, especially the lower legs and around the waist. The itching of flea bites 18 is caused by an allergic reaction. Sensitivity to flea bites varies between hosts 10. For example, children often have especially severe reactions to flea bites 10. In sensitive hosts 10, the bite 18 is often surrounded by a "halo" of red, irritated skin, as shown. Household pets, including cats and dogs, are common carriers of fleas. As illustrated, the human 10 host has sustained multiple bites 18 by a flea. In reaction to each bite 18, the host 10 has incurred an allergic reaction resulting in redness and swelling around each bite 18. In response to the itchiness of the bite 18, the host 10 will typically scratch the bites 18 causing open sores 20 that may become infected with bacteria and fungi.

Figure 3:
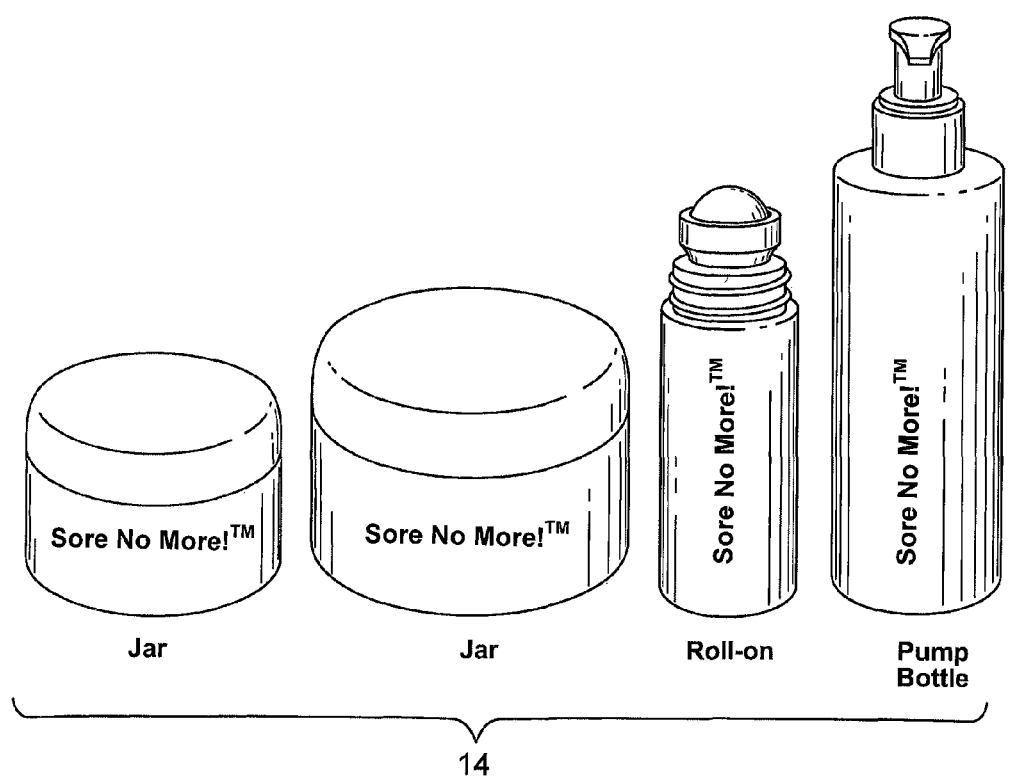
FIG. 3 illustrates various products sold under the trademark SORE NO MORE!™. (The SORE NO MORE!™ product is available from the www.sorenomore.com website at 150 East Center Street, Moab, Utah 84532.)

Referring now to FIG. 3, a product line of the Sore No More!™ product is shown. The product 14, sold under the trademark SORE NO MORE!™, comprises a formulation that rids a host of an unwanted foreign body. For example, in one embodiment, the SORE NO MORE!™ product 14 is applied to the scalp of a human host to rid the scalp of lice. In another embodiment, the SORE NO MORE!™ product 14 is applied to the body of a canine host to rid the canine of fleas. In yet another embodiment, the SORE NO MORE!™ product 14 is combined with a carpet shampoo to rid the carpet of fleas. In another embodiment, the SORE NO MORE!™ product 14 is combined with one or more surfactants to provide a cleansing agent for washing, or cleansing a host. In another embodiment, the SORE NO MORE!™ product 14 is provided in an aerosol form to fumigate an area.

The SORE NO MORE!™ product 14 is a composition comprising multiple chemical components. Specifically, the active components of the product 14 include 3% Menthol, 3% Camphor and 0.03% Capsacian. Additional components of the product 14 may include one or more of the following: aloe vera extract, carbomer, grapefruit seed extract, green tea extract, orange peel extract, queen of the prairie extract, vegetable glycerin, witch hazel, yucca extract, rose water, decyl polyglucose, deionized water, silica, and sodium hydroxymethyl glycinate. Specifics regarding the components of the composition 14 are included in Table 1.

TABLE 1

| Ingredient | Structural Formula | Function |
| --- | --- | --- |
| Menthol Molecular Formula: $C_{10}H_{20}O$ | | Obtained naturally from peppermint or other mint oils. It is used to give a cool feeling to the skin after application. It is also a very mild local anesthetic. |
| Camphor Molecular Formula: $C_{10}H_{16}O$ | | Derived from the wood of the camphor tree. It gives a cool feeling to the skin and works as a skin-conditioning agent. Have antiseptic and anesthetic properties. |
| Capsaicin Molecular Formula: $C_{11}H_{27}NO_3$ | | A stimulant, biological product that relieves aches and pains of arthritis by intercepting the pain signals sent to the brain due to inflamed joints. |
| Aloe Vera Extract | From the leaves of one or more of species of the aloe plant. Uses include treating burns and mild abrasions and are historically a strong skin-conditioning agent. | |
| Carbomer | It is a polymer of acrylic acid. Used to control the viscosity. | |
| Decyl Polyglucose | Derived from corn and fats of coconut and palm kernel oils. It is used as a surfactant. | |
| Vegetable Glycerin | A Polyhydric alcohol used as a humectant and skin-conditioning agent. | |
| Grapefruit Seed Extract | An organic anti-microbial and fungicidal agent that is non-corrosive and non-irritant to the skin. | |
| Green Tea Extract | Biological additive used as an anti-irritant. Rich in vitamin 'C' and fluoride, acting as a mild antibacterial agent. | |
| Orange Peel Extract | An extract from the rinds of oranges citrus sinensis with the properties of an anti-inflammatory biological additive. | |
| Queen of the Prairie Extract | Biological antiseptic containing high levels of salicylic acid. | |
| Rose water | An aqueous solution of the odoriferous species of flowers of *rosa centifolia*. | |
| Silica | An inorganic oxide working as an opacifying agent. | |
| Sodium | Sodium salt of the substituted amino acid for a preservative and neutralizer. | |

TABLE 1-continued

| Ingredient | Structural Formula | Function |
|---|---|---|
| Hydroxymethyl Deionized water | | Purified water to control viscosity. |
| Witch hazel | | An astringent obtained from *hamamelis virginiana*. |
| Yucca Extract | | A biological skin-conditioning agent derived from a select group of cactus in the Yucca family that is used to treat burns and mild abrasions by working as an anti-inflammatory agent and reducing erythema. |

A composition comprised of ingredients found in Table 1 may be applied to an infested host to eliminate foreign bodies. In addition to the ingredients of Table 1, components may be added to the composition to obtain a desired benefit. For example, in one embodiment an additional moisturizer is added to the composition to treat the irritated skin of the host. In another embodiment, an antibiotic is added to the composition to treat an infected sore of the host. In another embodiment, an analgesic is added to the composition to further soothe the irritated skin of the host. In another embodiment, essential oils are added to the composition to change the scent of the composition. In another embodiment, compressed, liquefied volatile gasses are added to the composition to provide an aerosol.

The composition 14 may include any beneficial combination of the abovementioned components. The composition 14 may be applied to infested, or affected areas of the host to rid the host of foreign bodies 12. The composition 14 may be in the form of, but not limited to, a gel, lotion or similar medium so it may be externally and topically applied. The composition 14 is applied so that it is absorbed by the foreign bodies 12. For example, the composition 14 is applied to the host by thoroughly rubbing the composition onto the affected area of the host. The composition 14 should remain on the infested area 10 until the foreign body 12 is killed. In one embodiment, the composition 14 is applied to the infested area for a period from about 30 seconds to about one hour. In another embodiment, the composition 14 is applied to the infested area for a period of time from about one minute to about fifteen minutes. In another embodiment, the composition 14 is applied to the infested area for a period of about 10 minutes.

The foreign host 12 is killed by the composition 14 during treatment of the infested area 10 with the composition 14. Specifically, the composition 14 terminates the foreign host 12 by two mechanism. First, the active ingredients of the composition 14 disrupt the cellular structure of the foreign host 12, leading to cellular death of the foreign host 12. Essentially, the composition 14 dissolves, or otherwise results in the deterioration of the body of the foreign host 12. The foreign host 12 is unable to resist the deterioration and thereby is killed. Second, the active ingredients of the composition 14 disrupt the respiration of the foreign host 12. As such, the composition 14 suffocates the foreign host 12 resulting in death to the foreign host 12.

Following treatment of the infested area with the composition 14, the affected or infested area 10 is rinsed with an appropriate rinsing agent. For example, where the composition 14 is water soluble, the composition 14 is removed from the treated host with water, or another liquid with properties similar to water. As the composition 14 is rinsed from the host 10, the killed foreign bodies 12 are removed with the composition 14 and the rinsing agent. Alternatively, the foreign bodies 12 may be removed by vacuuming the infested area, especially where the infested area is flooring, such as carpet.

Thus, as discussed herein, the embodiments of the present invention embrace compositions that eradicate foreign bodies from a host. In particular, at least some embodiments of the present invention relate to systems and methods for eliminating fleas, lice and other foreign bodies from humans, animals and/or other hosts where such foreign bodies reside.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for killing a foreign body selected from fleas, flea eggs, lice or lice eggs, on a host, the method comprising applying a composition to an area of the host infested with the foreign body, wherein said composition comprises 3% menthol, 3% camphor, and 0.03% capsaicin.

2. The method of claim 1, wherein the host is a mammal.

3. The method of claim 1, wherein the host is an animal.

4. The method of claim 1, wherein the host is not an animal.

5. The method of claim 1, wherein the composition is applied to the infested area of the host for about 10 minutes.

6. The method of claim 1, wherein the composition is incorporated into a product selected from the group consisting of: a shampoo, a detergent, a foam, a spray, a lotion, an aerosol, a conditioner, a moisturizer, a gel, a powder, and a balm.

7. The method of claim 1, wherein the composition includes at least one additional component selected from the group comprising: aloe vera extract; carbomer; decyl polyglucose; deionized water; grapefruit seed extract; green tea extract; orange peel extract; queen of the prairie extract; rose water; silica; sodium; hydroxymethyl glycinate; vegetable glycerin; witch hazel; and yucca extract.

8. The method of claim 7, wherein the host is a mammal.

9. The method of claim 7, wherein the host is an animal.

10. The method of claim 7, wherein the host is not an animal.

11. The method of claim 1, wherein the composition is applied to the infested area of the host for about 10 minutes.

12. The method of claim 11, wherein the composition kills the foreign body.

13. The method of claim 7, wherein the composition is incorporated into a product selected from the group consisting of: a shampoo, a detergent, a foam, a spray, a lotion, an aerosol, a conditioner, a moisturizer, a gel, a powder, and a balm.

14. A method for ridding a host of a foreign body wherein the foreign body is selected from fleas, flea eggs, lice or lice eggs, comprising:

applying a composition to an area of the host infested with the foreign body; soaking the infested area of the host with the composition for a period of time; and rinsing the infested area of the host with a rinsing agent, wherein the composition kills the foreign body, and rinsing the area with the rinsing agent removes the foreign body from the host; wherein the composition comprises 3% menthol, 3% camphor, and 0.03% capsaicin.

15. The method of claim 14, wherein the host is a mammal.

16. The method of claim 14, wherein the host is an animal.

17. The method of claim 14, wherein the host is not an animal.

18. The method of claim 14, wherein the infested area is soaked for about 10 minutes.

19. The method of claim 14, wherein the composition is incorporated into a product selected from the group consisting of: a shampoo, a detergent, a foam, a spray, a lotion, an aerosol, a conditioner, a moisturizer, a gel, a powder, and a balm.

20. The method of claim 14, wherein the composition includes at least one additional component selected from the group comprising: aloe vera extract, carbomer, grapefruit seed extract, green tea extract, orange peel extract, queen of the prairie extract, vegetable glycerin, witch hazel, yucca extract, rose water, decyl polyglucose, deionized water, silica, and sodium hydroxymethyl glycinate.

21. The method of claim 20, wherein the host is a mammal.

22. The method of claim 20, wherein the host is an animal.

23. The method of claim 20, wherein the host is not an animal.

24. The method of claim 20, wherein the foreign body is a parasite.

25. The method of claim 20, wherein the infested area is soaked for about 10 minutes.

26. The method of claim 20, wherein the composition is incorporated into a final product selected from the group comprising: a shampoo, a detergent, a foam, a spray, a lotion, an aerosol, a condition, a moisturizer, a gel, a powder, and a balm.

* * * * *